(12) United States Patent
Berookim

(10) Patent No.: US 12,154,668 B2
(45) Date of Patent: Nov. 26, 2024

(54) MEDICAL TEST RESULTS AND IDENTITY AUTHENTICATION SYSTEM AND METHOD

(71) Applicant: Mehron Berookim, Los Angeles, CA (US)

(72) Inventor: Mehron Berookim, Los Angeles, CA (US)

( * ) Notice: Subject to any disclaimer, the term of this patent is extended or adjusted under 35 U.S.C. 154(b) by 599 days.

(21) Appl. No.: 17/355,104

(22) Filed: Jun. 22, 2021

(65) Prior Publication Data
US 2022/0344015 A1 Oct. 27, 2022

Related U.S. Application Data

(60) Provisional application No. 63/179,126, filed on Apr. 23, 2021.

(51) Int. Cl.
*G16H 10/65* (2018.01)
*G06F 21/32* (2013.01)
(Continued)

(52) U.S. Cl.
CPC ............ *G16H 10/65* (2018.01); *G06F 21/32* (2013.01); *G06F 21/6245* (2013.01); *G06K 1/121* (2013.01); *G06K 19/06037* (2013.01); *G06K 19/06112* (2013.01); *G06Q 20/3558* (2013.01); *G06Q 40/02* (2013.01); *G06Q 50/265* (2013.01);
(Continued)

(58) Field of Classification Search
CPC ........ G16H 10/65; G16H 10/40; G16H 10/60; G06F 21/32; G06F 21/6245; G06K 1/121; G06K 19/06037; G06K 19/06112; G06Q 20/3558; G06Q 40/02; G06Q 50/265;
(Continued)

(56) References Cited

U.S. PATENT DOCUMENTS

| | | | |
|---|---|---|---|
| 2006/0293925 A1* | 12/2006 | Flom | G07C 9/257 707/999.009 |
| 2009/0177495 A1* | 7/2009 | Abousy | G16H 40/67 705/3 |
| 2016/0042126 A1* | 2/2016 | Walton, III | G16H 10/65 705/3 |

FOREIGN PATENT DOCUMENTS

CN 204480328 U * 7/2015

OTHER PUBLICATIONS

Perrin, Richard A. "Biometrics technology adds innovation to healthcare organization security systems." Healthcare Financial Management 56.3: 86(3). Healthcare Financial Management Association. (Mar. 2002)) (Year: 2002).*

\* cited by examiner

*Primary Examiner* — Linh Giang Le
(74) *Attorney, Agent, or Firm* — Jafari Law Group, Inc.

(57) ABSTRACT

A system and method that enables users to provide authenticated medical records (e.g., vaccination records, viral anti-body test results, etc.) to a third-party (e.g., a venue) to gain access to the third-party is provided. In this way, the third party may confirm that the user is sufficiently immune to a particular disease (e.g., COVID-19) and may thereby minimize the threat of the user introducing the contagious disease to the third party. The system includes a biometric data recognition system that authenticates the identity of a user, a medical records acquisition system that acquires the medical records of the authenticated user, and a system for the displaying or otherwise providing the medical records to the third-party for review. The system also includes a system identification card that includes the user's contact information, alphanumeric characters associated with the user's driver's license number, medical records of the user, and other elements.

18 Claims, 12 Drawing Sheets

(51) Int. Cl.
  *G06F 21/62* (2013.01)
  *G06K 1/12* (2006.01)
  *G06K 19/06* (2006.01)
  *G06Q 20/34* (2012.01)
  *G06Q 40/02* (2023.01)
  *G06Q 50/26* (2012.01)
  *G16H 10/40* (2018.01)
  *G06V 40/12* (2022.01)
  *G06V 40/16* (2022.01)

(52) U.S. Cl.
  CPC ......... *G16H 10/40* (2018.01); *G06V 40/1365* (2022.01); *G06V 40/172* (2022.01)

(58) Field of Classification Search
  CPC ............. G06Q 20/355; G06V 40/1365; G06V 40/172; G06V 10/95; G06V 30/1983
  See application file for complete search history.

MEDICAL TEST RESULTS AND IDENTITY AUTHENTICATION SYSTEM AND METHOD

PRIORITY NOTICE

The present application claims priority to U.S. Provisional Patent application with Ser. No. 63/179,126, filed on Apr. 23, 2021, the disclosure of which is incorporated herein by reference in its entirety.

FIELD OF THE INVENTION

This invention relates to a framework, system, and method for providing medical test results and identity authentication, including the real time authentication of an individual's identity and vaccination and/or viral antibody test results using biometric information and identification cards.

BACKGROUND

Precautionary screening measures are becoming commonplace to regulate access into venues such as businesses, restaurants, concerts, sporting events, hair salons, etc. Common screening measures include taking a person's body temperature to determine if he/she has a fever, requiring that each person wash his/her hands or use alcohol-based hand rub (ABHR) prior to entering, determining if a person has had contact with anyone with a confirmed infectious disease (e.g., COVID 19) in the last 14 days, etc.

However, such screening measures cannot guarantee that a person is free of a harmful virus, and if allowed access to the venue, may cause the spread of a harmful virus to other attendees.

Accordingly, there is a need for a medical test results and identity authentication system that authenticates the identity of a person while providing the person's medical records (e.g., proof of vaccination, viral antibody test results, etc.) in real time to a venue prior to allowing admittance of the individual.

SUMMARY

Summary to be provided upon approval of specification and claims.

BRIEF DESCRIPTION OF THE DRAWINGS

Other objects, features, and characteristics of the present invention as well as the methods of operation and functions of the related elements of structure, and the combination of parts and economies of manufacture, will become more apparent upon consideration of the following description and the appended claims with reference to the accompanying drawings, all of which form a part of this specification. None of the drawings are to scale unless Vs specifically stated otherwise.

DETAILED DESCRIPTION OF EXEMPLARY EMBODIMENTS

In general, the system according to exemplary embodiments hereof, provides a system and method that enables users to provide authenticated medical records (e.g., vaccination records, viral anti-body test results, etc.) to a third-party (e.g., a venue) to gain access to the third-party. Appropriately, the system may be referred to as a "vaccination passport". For example, a particular venue hosting a particular event may require that all attendees show proof of a particular vaccination and/or positive viral antibody test results before gaining entry to the event. In this way, the venue may minimize the threat of a contagious disease (e.g., a virus such as COVID-19) being introduced to the event and spread to the attendees.

Accordingly, this specification will describe the system predominantly in regard to two distinctly different types of users: (i) the consumer C desiring access to a venue, and (ii) the venue V desiring to authenticate the identity and medical records of the consumer C prior to granting him/her access.

It is understood that the consumer C may include any type of person wishing to gain access to any type of person, place, or thing, and that the venue V may include any type of person, place, or thing that the consumer C may wish to access. For example, a venue V may include (without limitation) any type of establishment, location, person, meeting, gathering, event, conference, and/or any other type of entity that may benefit from the screening process that the system 10 may provide, and a consumer C may include any type of person(s) wishing to gain access to any type of venue(s) V.

For the purposes of this specification, the system 10 will be described primarily in regard to authenticating a consumer's identity while providing the consumer's vaccination records, antibody test results, and/or other virus-related medical data to a venue V. However, it is understood that the system 10 may provide any type of information regarding a consumer C to a venue V, and that the system 10 is not limited in any way by the types of consumer information that it may retrieve, authenticate, and/or provide to a venue V.

Figure 1:
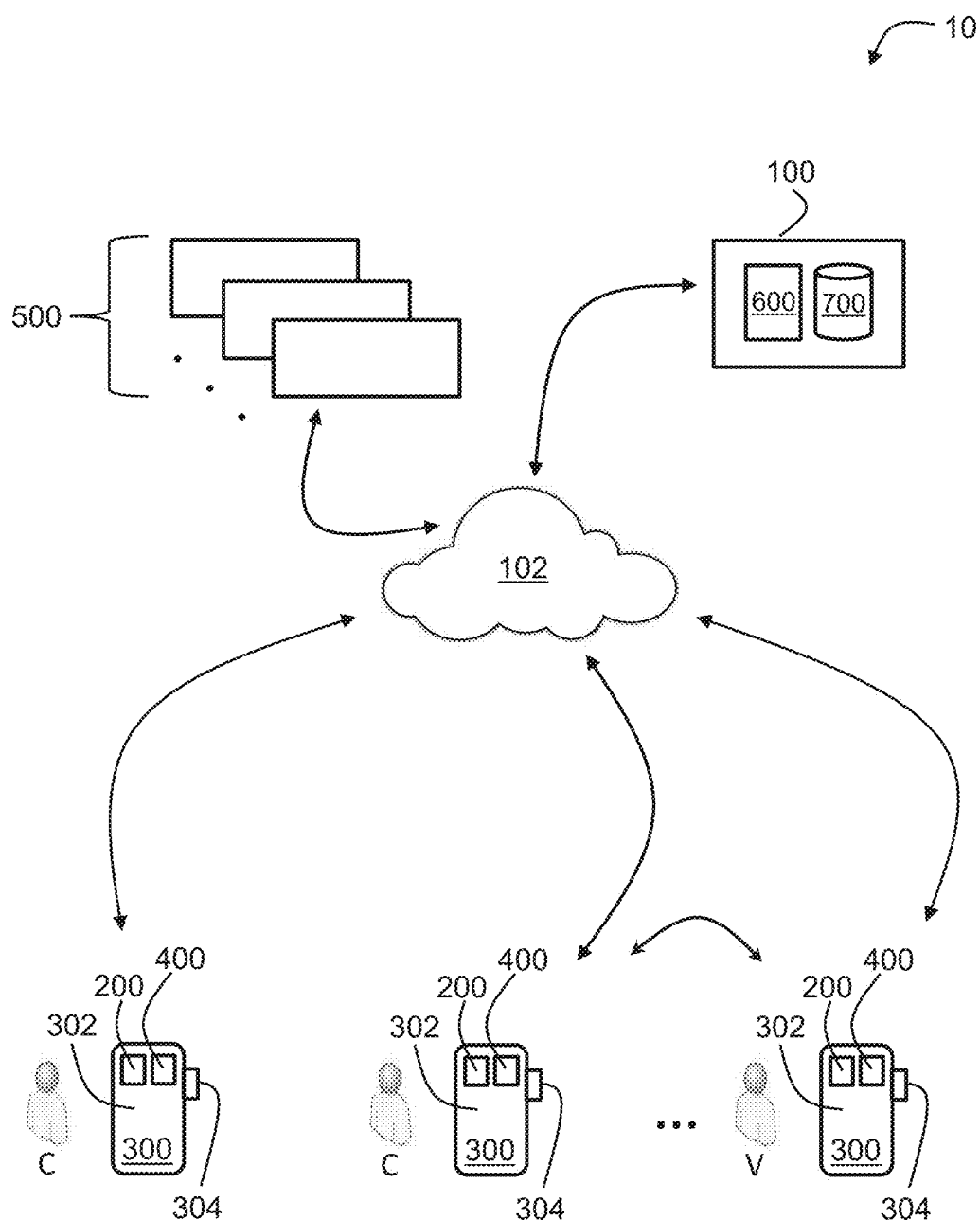
FIG. 1 shows an overview of a medical test results and identity authentication system in accordance with exemplary embodiments hereof.

FIG. 1 shows an overview of an exemplary framework for a medical test results and identity authentication system 10 (also referred to herein as simply the system 10) according to exemplary embodiments hereof. As shown, the medical test results and identity authentication system 10 may include a backend controller 100 that may interface with users C, V of the system 10 (individually and/or collectively) via one or more application interfaces 200 (e.g., a mobile application or "app", a browser, website or Internet interface, or other types of applications) running on one or more computing devices 300 (e.g., smart phones, tablet computers, laptops, desktop computers, mobile media players, etc.). While FIG. 1 shows two consumers C and one venue V, it is understood that the system 10 may interface with any number of consumers C and/or any number of venues V at any time. The system 10 also may include a biometric recognition system 400 as well as other systems, elements and components as required by the system 10 to fulfill its functionalities.

In some embodiments, the computing devices 300 (e.g., the smartphones 300 used by a consumer C and/or by a venue V) may preferably include a touchscreen 302 and/or a camera 304.

The system 10 may interface with various external entities and/or systems 500 such as hospitals, medical offices, medical clinics, insurance providers, virus test providers, virus antibody test providers, vaccination providers, any other type of entities that may provide required information (e.g., any type of medical record providers), and any combinations thereof. In this way, the system 10 may retrieve information from and share information with the external systems 500 (preferably in real time) during use of the system 10 and as the system 10 performs its functionalities. This will be described in detail in other sections.

The backend system 100 includes one or more servers 104 including one or more software systems 106, one or more applications 600, and one or more databases 700. The one or more software systems 106 may include operating systems, system software, web server software, social networking software, communication software, software applications, scripts, firmware, other types of software systems and any combinations thereof. The applications 600 and databases 700 will be described in other sections.

In exemplary embodiments, personal information stored and exchanged within the system is secured using known technologies, for example blockchain technologies may be employed to keep patient information secured.

The computing devices 300 and the backend controller 100 may preferably be connected to one or more networks 102 (e.g., the Internet, LAN, WAN, wireless communication systems, cellular communication systems, telephony or other types of communication systems or protocols) and may communicate thereby. In some embodiments, the backend controller 100 may include a cloud platform (e.g., one or more backend servers), one or more local controllers, or any combination thereof. In some embodiments, the backend controller 100 includes a cloud platform that interfaces with one or more local controllers. For example, administrators A of the system 10 may interface with the system 10 via a local controller in communication to a cloud platform.

In some embodiments, the mobile application 200 ("app") provides a graphical user interface (GUI) that enables a user C, V to interface with the application 200, the backend 100, and the overall system 10. The application 200 may generally provide an interface with which the user C, V may enter information for the system 10 to utilize (e.g., upload to the backend 100), and interface controls (e.g., touchscreen buttons, etc.) for a user C, V to activate while interacting with the system 10. The application 200 also may display data and other types of information that a user C, V may read or otherwise consume and/or provide to other users C, V. In general, and in some embodiments, the application 200 may provide a primary interface with which a user C, V may interact with the system 10.

In some embodiments, the biometric recognition system 400 includes, without limitation, a facial recognition application 402 that may interface with the device's camera 304, a fingerprint recognition application 404 that may interface with the device's touchscreen 302, and/or any other suitable biometric recognition application running on the user's device 300 and/or on the backend 100.

Figure 2:
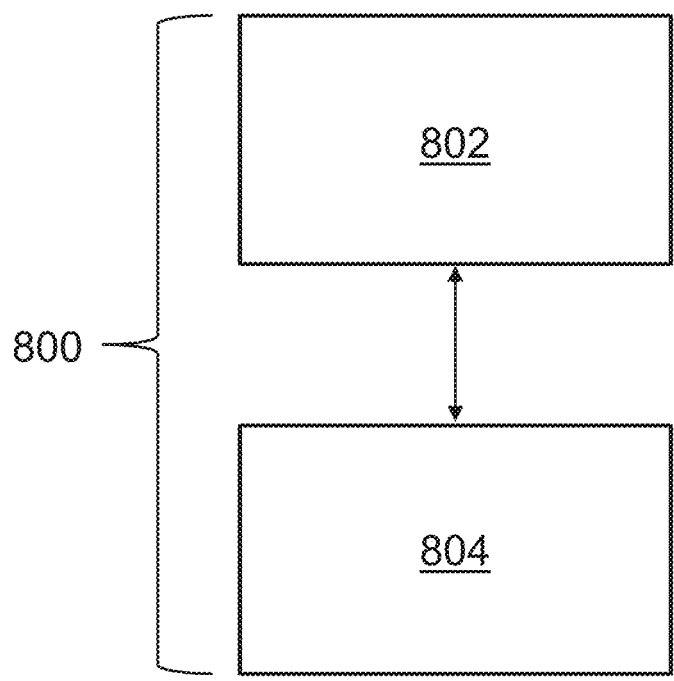
FIG. 2 shows example workflow actions taken by a medical test results and identity authentication system in accordance with exemplary embodiments hereof.

In some embodiments as shown in FIG. 2, the system 10 may generally perform acts 800 associated with two phases of operation (without limitation):

Phase 1: At 802, (i) register and authenticate the identity of a potential consumer C for use with the system 10, (ii) receive biometric data from the consumer C for use during Phase 2, and (iii) interface with external systems 500 to acquire medical records associated with the consumer C. Alternatively, the system 10 may acquire the medical records during Phase 2; and Phase 2: At 804, utilize the information received in Phase 1 to authenticate the consumer C in real time (onsite) prior to gaining access to a venue V. The system 10 also may acquire the consumer's medical records during this Phase 2.

Figure 3:
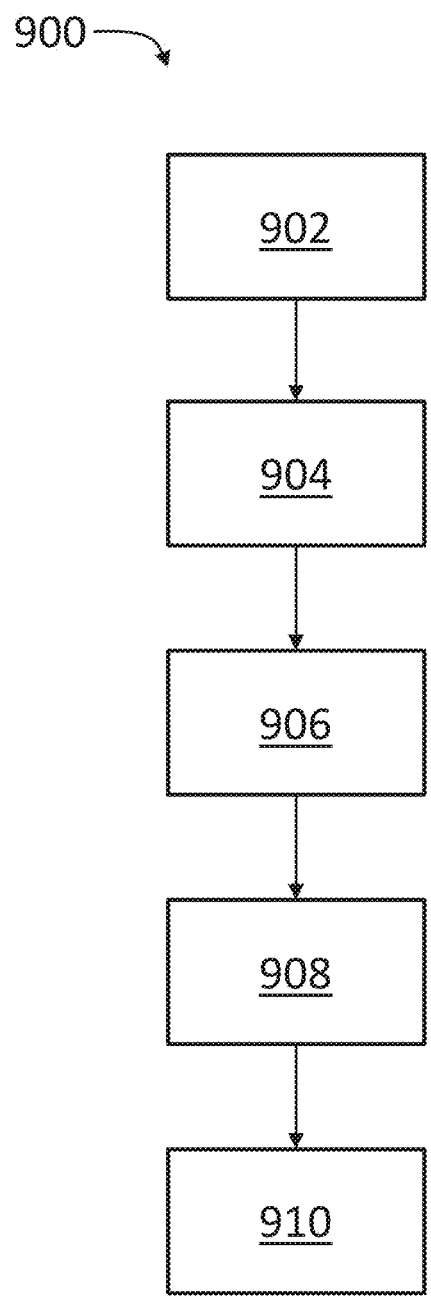
FIG. 3 shows example workflow actions taken by a medical test results and identity authentication system in accordance with exemplary embodiments hereof.

In some embodiments as shown in FIG. 3, Phase 1 may generally include the acts 900 outlined below (without limitation). Note that these acts generally register a potential consumer C with the system 10 (create a user profile) and are performed prior to a consumer C attempting to use the system 10 to gain access to a venue V.

1. At 902, authenticate the identity of the consumer C and create his/her system profile.
2. At 904, receive and authenticate biometric data from the consumer C;
2. At 906, associate the authenticated biometric data with the consumer's system profile and store the data into a database 700;
3. At 908, receive medical records for a particular consumer C from an external system 500; and
4. At 910, associate the medical records with the consumer's system profile and with the consumer's biometric data and store the medical records in a database 700.

Note that actions 908 and 910 may alternatively be performed during Phase 2.

Figure 4:
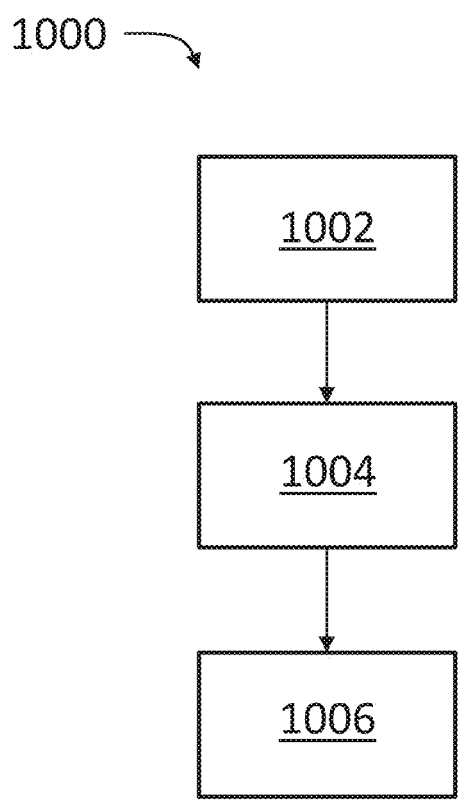
FIG. 4 shows example workflow actions taken by a medical test results and identity authentication system in accordance with exemplary embodiments hereof.

In some embodiments as shown in FIG. 4, Phase 2 may generally include the acts 1000 outlined below (without limitation). Note that these acts are generally used to authenticate the identity of a consumer C and his/her medical records (in real time and onsite) prior to being granted access to a venue V.

1. At 1002, receive real time biometric data from the consumer C (e.g., a fingerprint or facial image while at the venue V attempting to gain access);
2. At 1004, compare the biometric data received in (1) to the authenticated biometric data received in Phase 1, and upon determining a match, authenticating the identity of the consumer C;
3. If the consumer's identity is authenticated, at 1006 retrieve the medical records associated with the consumer C and provide the records and the proof of identity to a venue V to gain access. Note that the medical record may be retrieved from a database 700 if the system 10 acquired the records from an external system 500 during Phase 1, and/or from an external system 500 if the system 10 did not.

It is understood that the actions 800, 900, 1000 described above are for demonstration and that the system 10 may perform additional acts, may not perform all of the described acts, and/or may perform any acts in other order.

Phase 1 and Phase 2 will next be described in further detail.

Phase 1

Figure 5:
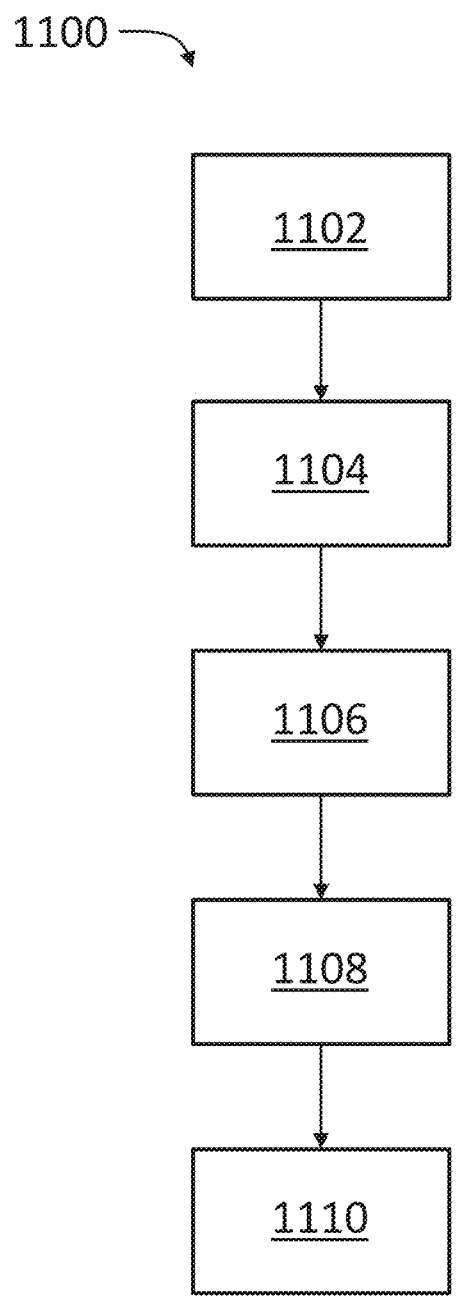
FIG. 5 shows example workflow actions taken by a medical test results and identity authentication system in accordance with exemplary embodiments hereof.

In some embodiments as shown in FIG. 5, the system 10 performs actions 1100 during Phase 1. At 1102, the system 10 may first authenticate the identity of the consumer C by receiving images of the consumer's government approved identification card (e.g., a passport, a driver's license, a Real ID, etc.), by receiving correct answers to security questions posed to the consumer C by the system 10, by verifying the consumer's address and mailing the consumer C a personal identification number (PIN) that is then entered into the system 10, and/or by other identification verification techniques as known in the art.

Once the system 10 has verified the identity of the consumer C, the consumer C may upload biometric data to the system 10 at 1104. This may include, without limitations, facial images of the consumer C (e.g., taken by the device's camera 304), fingerprint images of the consumer C (e.g., scanned using the device's touchscreen 302), and/or other types of biometric data associated with the consumer C. This information is received by the system 10, associated with the consumer's system profile, and stored to a database 700 at 1106. This information also may be compared to information residing on the consumer's identification card to further authenticate the validity of the information. For example, a facial image provided by the consumer C may be compared to the facial image displayed on the consumer's identification card to authenticate the provided facial image. In another example, the fingerprint image provided by the consumer C may be compared to the fingerprint displayed on the consumer's identification card to authenticate the provided fingerprint image.

As will be described in other sections, the system 10 may use this biometric information to authenticate the identity of the consumer C at a future moment in time (e.g., while attempting to gain entrance to a venue V). That is, the system 10 may compare authenticated biometric information provided during Phase 1 to biometric information provided at a later moment in time (e.g., at the venue V) to authenticate the identity of the consumer C.

Next, at 1108, the system 10 interfaces with one or more external systems 500 to receive the registered consumer's required medical information. This medical information preferably includes vaccination records (e.g., COVID-19 vaccination records), viral antibody test results (e.g., COVID-19 antibody test results), and/or any other type of pertinent medical records required by the system 10. It is preferable that the medical records include all pertinent information such as date(s) of any vaccinations and/or antibody tests, type(s) of vaccinations and/or antibody tests, expiration dates, the entity that supplied and/or performed the vaccinations and/or the antibody tests, and any additional information required by the system 10. Once received, the medical records are associated with the consumer's system profile and stored into a database 700 at 1110.

Note that in some embodiments, the actions 1108 and/or 1110 may be performed during Phase 2.

It is understood that the actions 1100 described above are for demonstration and that the system 10 may perform additional acts, may not perform all of the described acts, and/or may perform any acts in other order.

Phase 2

In some embodiments, once a consumer's identity has been authenticated and the system 10 has received and stored the consumer's medical records (e.g., Phase 1 has been completed), the system 10 may be used to authenticate the consumer's identity (onsite) while simultaneously providing a venue V the relevant medical record information. In this way, the consumer C may be granted access to the venue V.

As described below, the onsite authentication of the consumer C may be performed using (i) the consumer's device 300, (ii) the venue's device 300, and/or (iii) any combinations thereof.

Figure 6:
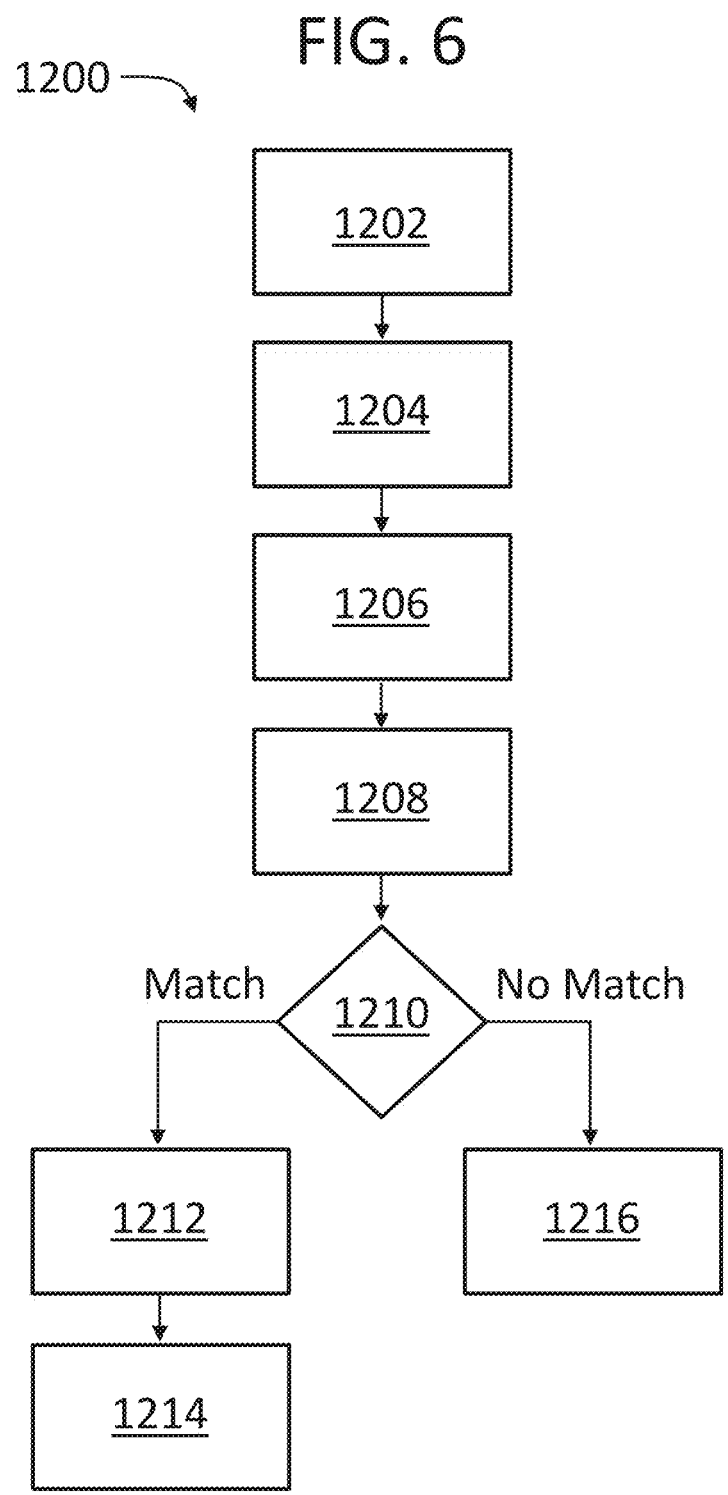
FIG. 6 shows example workflow actions taken by a medical test results and identity authentication system in accordance with exemplary embodiments hereof.
Figure 7:
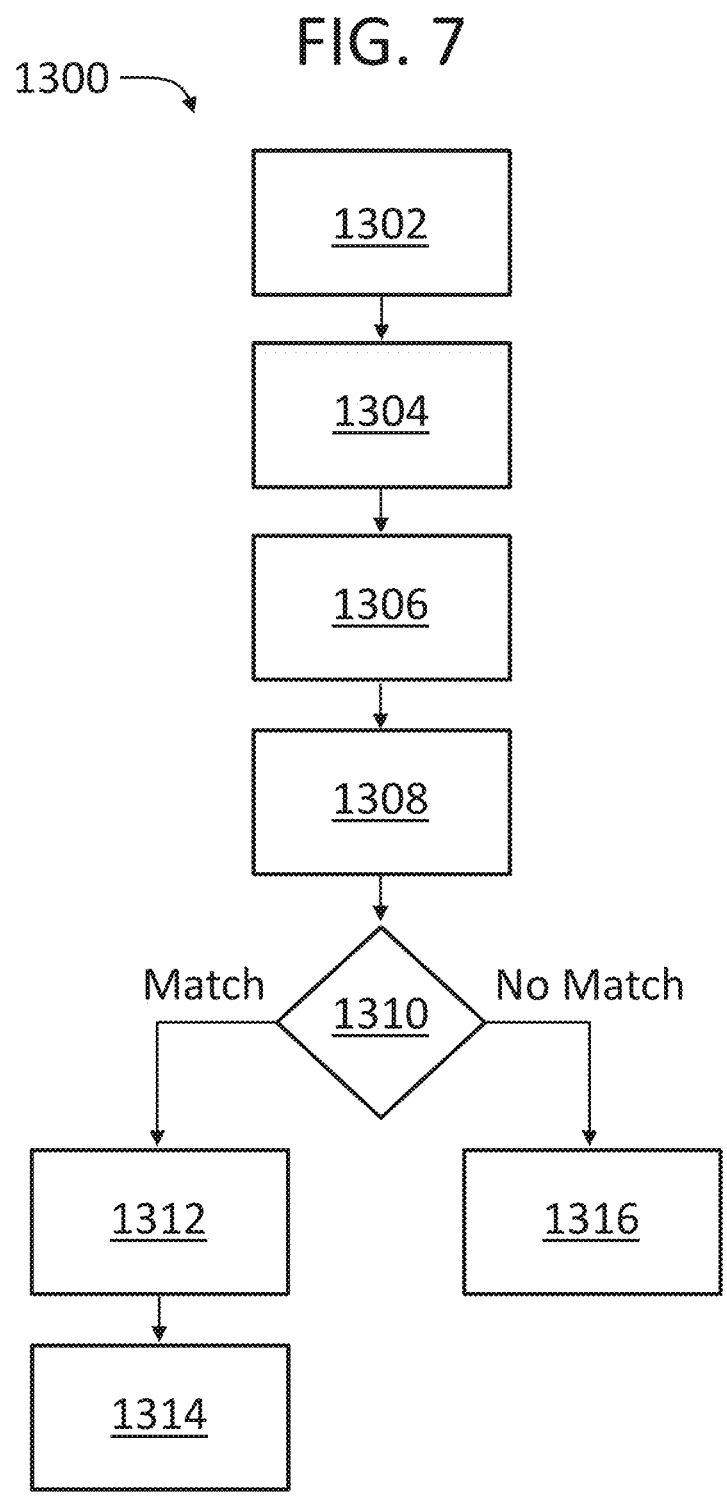
FIG. 7 shows example workflow actions taken by a medical test results and identity authentication system in accordance with exemplary embodiments hereof.

In some embodiments as shown in FIGS. 6-7, the onsite identity authentication is performed by actions using the consumer's device 300 running the application 200. In this scenario, the consumer C may launch the application 200 on his/her device 300, and the application 200 may require the consumer C to provide real time biometric data, including, e.g., a fingerprint, a facial image, etc., to his/her device 300 in that moment.

In a first example of actions 1200 as shown in FIG. 6, at 1202 the application 200 running on the consumer's device 300 may present the consumer C with an area on the device's touchscreen 302 to receive the consumer's fingerprint. The consumer C may press his/her finger onto the designated area at 1204 and the application 200 may scan or otherwise read the fingerprint. The fingerprint information may then be uploaded to the backend 100 at 1206 and compared to the corresponding fingerprint information acquired during Phase 1 at 1208 using the system's fingerprint recognition system 404.

If, at 1210, the newly uploaded fingerprint information matches the prior fingerprint information acquired in Phase 1, the system 10 may authenticate the identity of the consumer C at 1212. The system 10 may then access the consumer's system profile on the backend 100, obtain the pertinent medical records, and provide the records to the venue V for review at 1214. In addition, if the medical records were not acquired from external systems 500 during Phase 1, the system 10 may interface with the external systems 500 and retrieve the records at 1214 prior to providing the records to the venue V for review.

If, however, the newly uploaded fingerprint information does not match the prior fingerprint information acquired in Phase 1 at 1210, the system 10 may not validate the consumer's identity and the process may end at 1216.

In a second example of identity authentication actions 1300 as shown in FIG. 7, at 1302 the application 200 may launch the device's camera and request that the consumer C aim the camera at his/her face and acquire a facial image. The facial image may then be taken at 1304, uploaded to the backend 100 at 1306, and compared to the corresponding facial image acquired in Phase 1 at 1308 using the system's facial recognition system 402.

If, at 1310, the newly uploaded facial image matches the prior facial image acquired in Phase 1, the system 10 may authenticate the identity of the consumer C at 1312 and access the consumer's system profile on the backend 100, obtain the pertinent medical records, and provide the records for review at 1314. In addition, if the medical records were not acquired from external systems 500 during Phase 1, the system 10 may interface with the external systems 500 and retrieve the records at 1314 prior to providing the records to the venue V for review.

If, however, the newly uploaded facial image does not match the prior facial image acquired in Phase 1, the system 10 may not validate the consumer's identity and the process may end at 1316.

It is understood that the actions 1200, 1300 described above are for demonstration and that the system 10 may perform additional acts, may not perform all of the described acts, and/or may perform any acts in other order.

In some embodiments, during the actions 1214 (FIG. 6) and/or 1314 (FIG. 7) the system 10 may present the pertinent medical records on the display of the consumer's device 300 (e.g., on a GUI) and the consumer C may simply show the displayed records to the venue V. The venue V may then review/read the medical records and make a determination whether to grant the consumer C access or not.

In other embodiments during the actions 1214 (FIG. 6) and/or 1314 (FIG. 7), the system 10 may provide and present a quick response (QR) code on the display of the consumer's device 300 that the venue V may scan (using a camera 304 on the venue device 300 or the like). The system 10 may then direct the venue's device 300 to a website that provides the necessary medical records for admittance. Alternatively, scanning the QR code may initiate a download of the medical records to the venue's device 300. It is understood that the system 10 may provide the medical records using the consumer's device 300 using any suitable techniques and that the scope of the system 10 is not limited in any way by the way in which it provides the medical records to the venue V.

Figure 8:
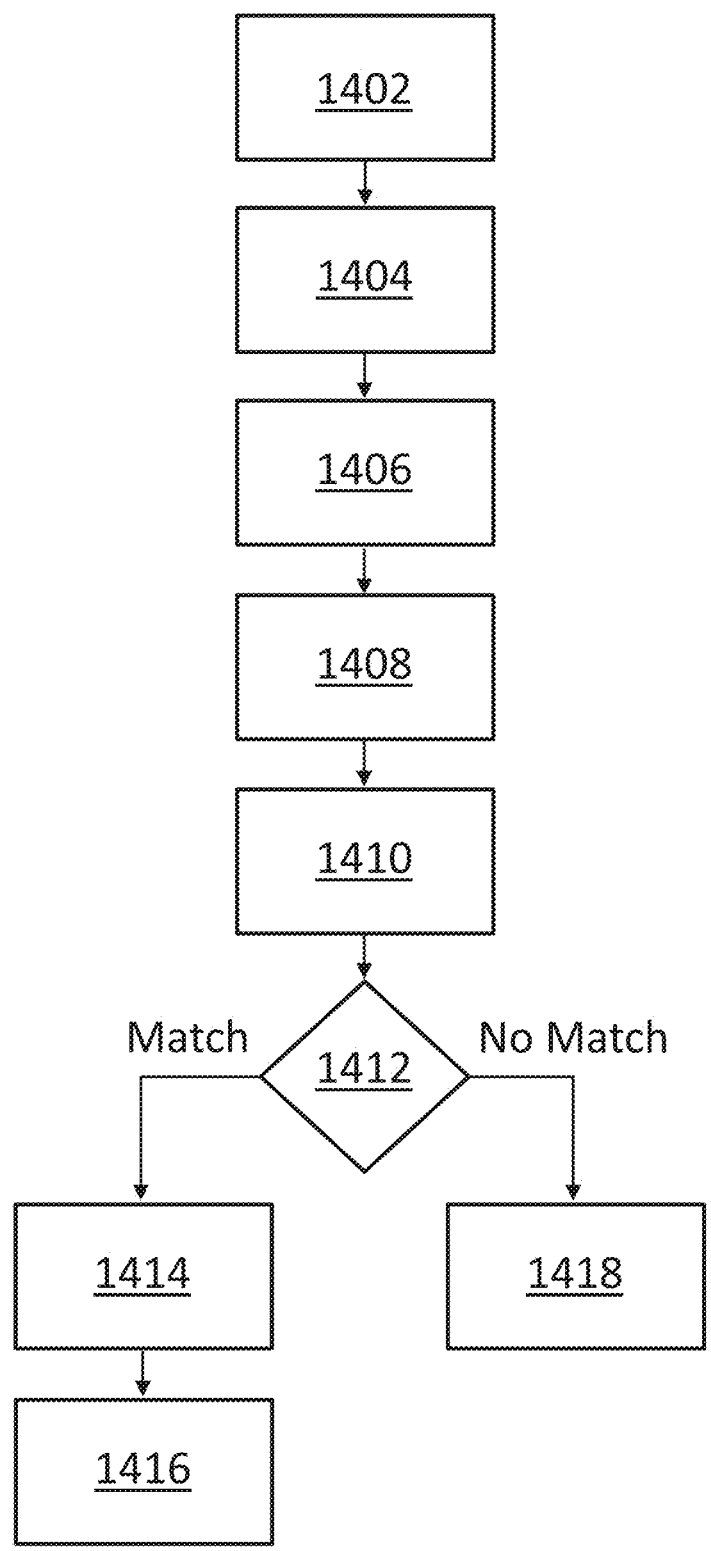
FIG. 8 shows example workflow actions taken by a medical test results and identity authentication system in accordance with exemplary embodiments hereof.
Figure 9:
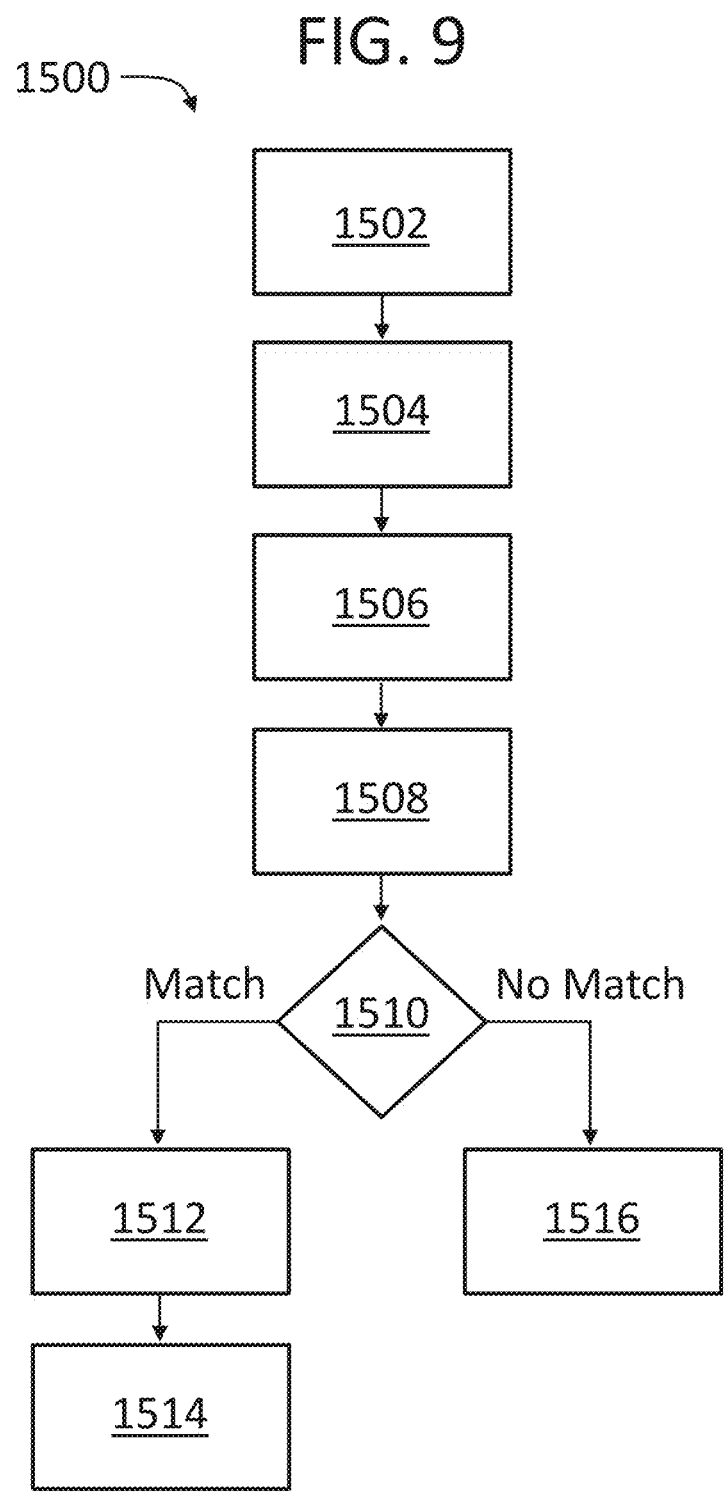
FIG. 9 shows example workflow actions taken by a medical test results and identity authentication system in accordance with exemplary embodiments hereof.

In some embodiments as shown in FIGS. 8-9, the onsite identity authentication is performed by actions using the venue's device 300 running the application 200. In this scenario, the venue V may launch the application 200 on his/her device 300, and the application 200 may require the consumer C to provide his/her name (e.g., using a passport, valid driver's license, etc.) and subsequent real time biometric data, including, e.g., a fingerprint, a facial image, etc., to the venue's device 300 in that moment.

In a first example of actions 1400 as shown in FIG. 8, at 1402 the application 200 running on the venue's device 300 may first request the legal name of the consumer C. The venue V may ask the consumer C for an identification card (e.g., driver's license, passport, and/or other identification card), and may scan the identification card using his/her venue device 300. Alternatively, the venue V may simply review the identification card and enter the consumer's name into the GUI of the application 200.

Once the consumer's identity has been entered, the application 200 at 1404 may present the consumer C with an area on the venue's device's touchscreen 302 to receive the consumer's fingerprint. The consumer C may press his/her finger onto the designated area at 1406 and the application 200 may scan or otherwise read the fingerprint. The fingerprint information may then be uploaded to the backend 100 at 1408, and using the consumer's name entered prior, the system 10 may access the consumer's system profile and compare the newly uploaded fingerprint information to the corresponding fingerprint information acquired during Phase 1 at 1410 using the system's fingerprint recognition system 404.

If, at 1412, the newly uploaded fingerprint information matches the prior fingerprint information acquired in Phase 1, the system 10 may authenticate the identity of the consumer C at 1414 and access the consumer's system profile on the backend 100, obtain the pertinent medical records, and provide the records for review at 1416. In addition, if the medical records were not acquired from external systems 500 during Phase 1, the system 10 may interface with the external systems 500 and retrieve the records at 1416 prior to providing the records to the venue V for review.

If, however, the newly uploaded fingerprint information does not match the prior fingerprint information acquired in Phase 1, the system 10 may not validate the consumer's identity and the process may end at 1418.

In a second example of identity authentication actions 1500 as shown in FIG. 9, once the consumer's name has been entered, the application 200 at 1502 may launch the venue's device's camera and request that the venue V aim the camera at the consumer's face and acquire a facial image of the consumer C. The facial image may then be taken at 1504, uploaded to the backend 100 at 1506 and compared to the corresponding facial image acquired in Phase 1 at 1508 using the system's facial recognition system 402.

If, at 1510, the newly uploaded facial image matches the prior facial image acquired in Phase 1, the system 10 may authenticate the identity of the consumer C at 1512 and access the consumer's system profile on the backend 100, obtain the pertinent medical records, and provide the records for review at 1514. In addition, if the medical records were not acquired from external systems 500 during Phase 1, the system 10 may interface with the external systems 500 and retrieve the records at 1514 prior to providing the records to the venue V for review.

If, however, the newly uploaded facial image does not match the prior facial image acquired in Phase 1, the system 10 may not validate the consumer's identity and the process may end at 1516.

In some embodiments during the actions 1416 and/or 1514, the system 10 may present the pertinent medical records on the display of the venue's device 300 (e.g., on a GUI) and the venue V may review the records to make a determination whether to grant the consumer C access or not. It is understood that the system 10 may provide the medical records using the venue's device 300 using any suitable techniques and that the scope of the system 10 is not limited in any way by the way in which it provides the medical records to the venue V.

It is understood that the actions 1400, 1500 described above are for demonstration and that the system 10 may perform additional acts, may not perform all of the described acts, and/or may perform any acts in other order.

In any of the embodiments described herein or otherwise, the system 10 preferably uses suitable data encryption as is known in the art while interfacing with the external systems 500, the consumer C, the venue V, and/or during any other communications, as necessary.

In any of the embodiments described herein or otherwise, it is understood that some actions 800, 900, 1000, 1100, 1200, 1300, 1400, 1500 may be taken by the system's backend 100, the system's application 200, and/or using any combination of the backend 100 and application 200. For example, the system's biometric recognition system 400 may reside on the backend 100, on the application 200, and/or on any combinations thereof, and actions taken by the system 400 may be taken on the backend 100, on the application 200, and/or on any combination thereof.

System Structure

Figure 10:
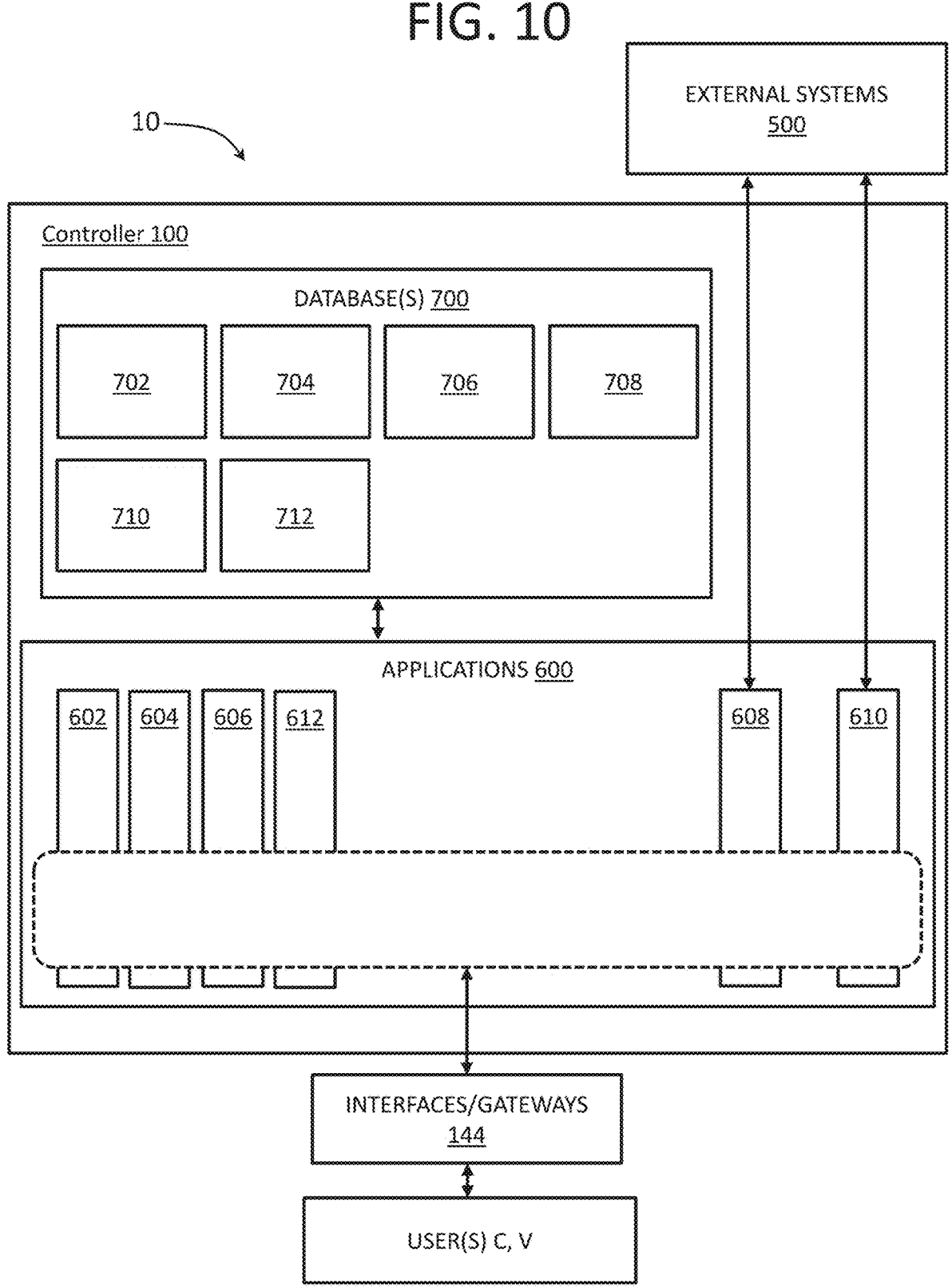
FIG. 10 shows aspects of a medical test results and identity authentication system computing environment in accordance with exemplary embodiments hereof.

FIG. 10 shows aspects of an exemplary medical test results and identity authentication system 10 of FIG. 1. As shown, the system 10 and backend system 100 comprises various internal applications 600 and one or more databases 700, described in greater detail below. The internal applications 600 may generally interact with the one or more databases 700 and the data stored therein.

The database(s) 700 may comprise one or more separate or integrated databases, at least some of which may be distributed. The database(s) 700 may be implemented in any manner, and, when made up of more than one database, the various databases need not all be implemented in the same way. It should be appreciated that the system is not limited by the nature or location of database(s) 700 or by the manner in which they are implemented.

Each of the internal applications 600 may provide one or more services via an appropriate interface. Although shown as separate applications 600 for the sake of this description, it is appreciated that some or all of the various applications 600 may be combined. The various applications 600 may be implemented in any manner and need not all be implemented in the same way (e.g., using the same software languages, interfaces or protocols).

In some embodiments, the applications 600 may include one or more of the following applications 600:

1. Registration and authentication application(s) 602. This application may receive identity information from the consumer C, authenticate the identity of the consumer C, receive biometric information from the consumer C, authenticate the biometric information, create a consumer's system profile, and perform other actions, as necessary. This application also may receive registration information from a venue V and create a venue's system profile.
2. Facial recognition application(s) 604. Note that the facial recognition application 604 may correlate with the facial recognition application 402 described in other sections.
3. Fingerprint recognition application(s) 606. Note that the fingerprint recognition application 606 may correlate with the fingerprint recognition application 404.
4. Data input application(s) 608. This application may receive any type of input data from any applicable system and/or element such as the application 200, the mobile device 300, the external system(s) 500, any other system and/or element and any combination thereof.
5. Data output applications(s) 610. This application may output any type of output data to any applicable system and/or element such as the application 200, the mobile device 300, the external system(s) 500, any other system and/or element and any combination thereof.
6. Data reporting application(s) 612. This application may generate any type of report regarding the use and/or functionalities of the system 10 including the identities of consumers C allowed access to particular venues V, statistical information, historical data, any other types of data and/or information and any combination thereof.

The applications 600 also may include other applications and/or auxiliary applications (not shown). Those of ordinary skill in the art will appreciate and understand, upon reading this description, that the above list of applications is meant for demonstration and that the system 10 may include other applications that may be necessary for the system 10 to generally perform its functionalities as described in this specification. In addition, as should be appreciated, embodiments or implementations of the system 10 need not include all of the applications listed, and that some or all of the applications may be optional. It also is understood that the scope of the system 10 is not limited in any way by the applications that it may include.

In some embodiments, the database(s) 700 may include one or more of the following databases:

1. Consumer profile database(s) 702. This database may store any data and/or other types of information related to a consumer C.
2. Venue profile database(s) 704. This database may store any data and/or other types of information related to a venue V.
3. Facial recognition database(s) 706. This database may store any data and/or other types of information related to and/or required by the facial recognition application 802 (402). For example, the database 706 may include information regarding different target persons required to be recognized by the system 10.
4. Fingerprint recognition database(s) 708. This database may store any data and/or other types of information related to and/or required by the fingerprint recognition application 804 (404). For example, the database 708 may include information regarding different target persons required to be recognized by the system 10.
5. Historical data database(s) 710. This database may store any and/or all historical data acquired by the system 10, including but not limited to, consumer data, venue data, and any other information as required.
6. Data report(s) database(s) 712. This database may store any reports of any kind generated by the system 10.

It is understood that the above list of databases is meant for demonstration and that the system 10 may include some or all of the databases, and also may include additional databases as required. It also is understood that the scope of the system 10 is not limited in any way by the databases that it may include.

Various applications 600 and databases 700 in the medical test results and identity authentication system 10 may be accessible via interface(s) 142. These interfaces 142 may be provided in the form of APIs or the like and made accessible to users C, V via one or more gateways and interfaces 144 (e.g., via a web-based application 200 and/or a mobile application 200 running on a user's device 300).

System Identification Card 1700

Figure 12:
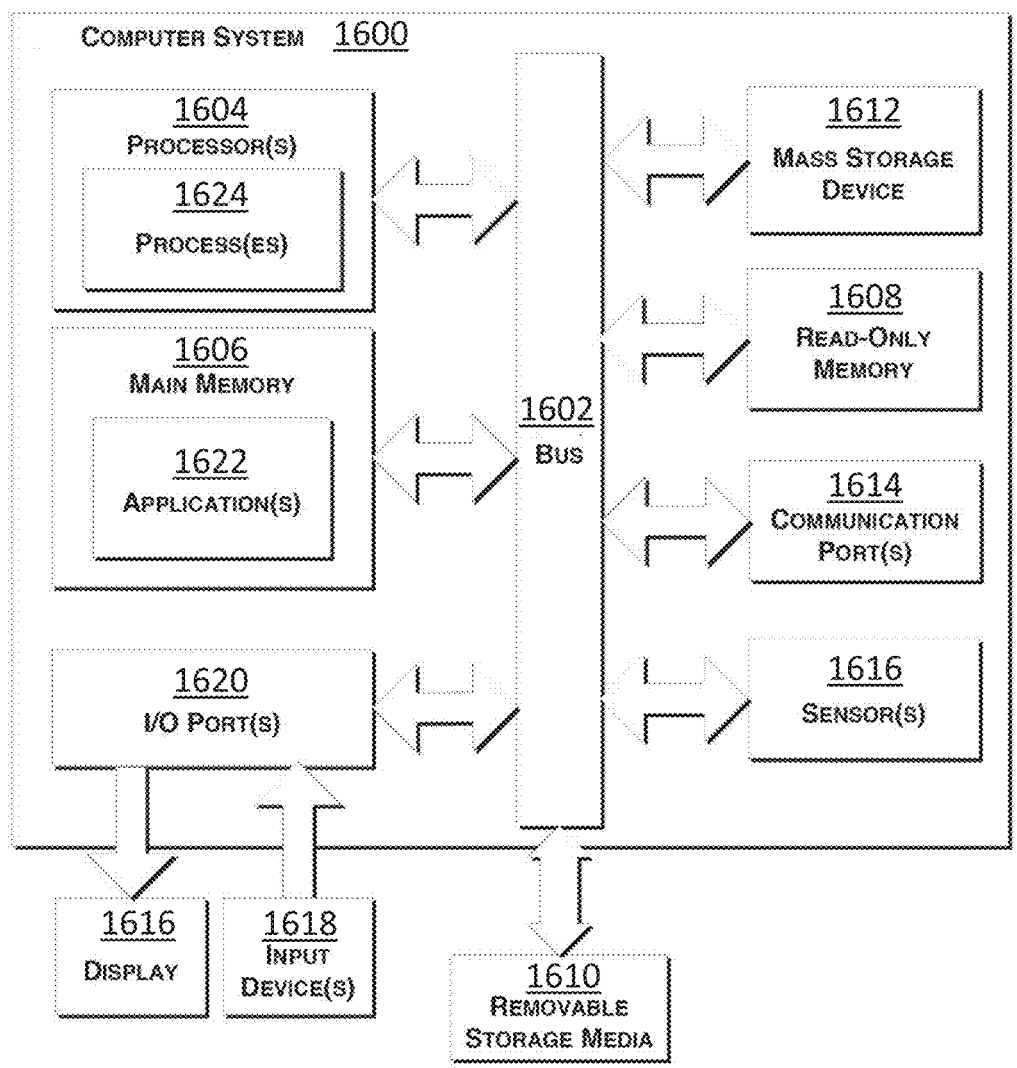
FIG. 12 depicts aspects of computing and computer devices in accordance with exemplary embodiments hereof.

FIG. 12 shows aspects of a further embodiment of the medical test results and identity authentication system 10. In some embodiments, the system 10 also includes a system identification card 1700 that may be issued to a particular customer C at a point in time after he/she has (i) received a new vaccination, (ii) has taken a new viral anti-body test and has received the results, (iii) has received other medical information of interest, and/or (iv) any combinations thereof. As described below, the system identification card 1700 includes information that identifies the customer C as well as medical information applicable for allowing the customer C access to a venue V. Note that while the card 1700 is predominantly described as a plastic identification card, the card 1700 also may include key fobs and other types of suitable cards.

As shown in FIG. 12, the system identification card 1700 may include the name and contact information 1702 of the customer C, an image 1704 of the customer C (preferably his/her face for easy identification), one or more alphanumeric characters 1706 (e.g., a character string) related to the customer's government issued identification card (e.g., driver's license, passport, Real ID, etc.), a system identification code 1708, other identifying information such as date of birth 1710, medical information 1712 (e.g., vaccination information, viral anti-body test results, etc. as described in other sections), a QR code 1714 (and/or other type of graphical code), an embedded microchip 1716 and associated contact plate, a magnetic stripe 1718 (e.g., on the card's back side), and other appropriate elements.

In some embodiments, the alphanumeric characters 1706 include one or more characters taken from the customer's state issued driver's license. For example, the alphanumeric characters 1706 may include the last 4 digits of the customer's driver's license. During use, a customer C may present his/her identification card 1700 and driver's license to a venue V for review. The venue V may compare the contact information 1702 and photograph 1704 of the customer C on the system card 1700 to the contact information and photograph of the customer C on the driver's license for confirmation of the customer's identity. The venue V also may compare the characters 1706 on the system card 1700 to the corresponding characters on the customer's driver's license to further authenticate the customer C. Upon such authentication, the venue V may then review the medical information 1712 on the system card 1700 to determine whether or not the customer C meets the vaccination and/or medical tests result requirements for access to the venue V.

In some embodiments, the QR code 1714 is similar to the QR code presented by the system 10 on the display of the customer's device during action 1214 (FIG. 6) and/or action 1314 (FIG. 7) as described above. The venue V may scan the QR code 1714 (e.g., using a camera 304 on the venue device 300 or the like) and the system 10 may direct the venue's device 300 to a website that provides the necessary medical records for admittance. Alternatively, scanning the QR code 1714 may initiate a download of the medical records to the venue's device 300.

In some embodiments, the embedded microchip 1716 provides the card 1700 with smartcard functionalities as is known in the art. The microchip 1716 also preferably includes internal memory that may store customer information such as, without limitation, the customer's medical information required for access to the venue V. The microchip 1716 also preferably provides other on-card functionalities such as, without limitation, encryption, and mutual authentication. During use, the vendor V may insert the customer's system card 1700 into a card reader to interface with the chip 1716 and to access the chip's stored information.

In some embodiments, the chip 1716 may include a contactless smartcard chip with an internal antenna that may communicate with a card reader through a contactless radio frequency (RF) interface (or through other suitable wireless technology protocols). It may be preferable that the chip 1716 conform to international smartcard standards (e.g., ISO/IEC 7816 and ISO/IEC 14443).

In some embodiments, the chip 1716 may update its stored information (e.g., the customer's medical information) upon the availability of new information. For example, when the customer C receives a new vaccination, the system 10 may interface with the chip 1716 (e.g., through a card reader, wirelessly, etc.) and update the customer's information to reflect the new vaccination. In this way, the system card 1700 may be updated in real time to include the most recent information regarding the customer C.

In some embodiments, the medical information 1712 is displayed on an electronic display embedded with the card 1700 (e.g., an LCD digital readout controlled by the embedded microchip 1716). In this way, the chip 1716 may be updated with the most recent customer information and may in turn control the display to show the most recent medical information for the venue V to review during use.

In some embodiments, the customer's medical information is encoded onto the magnetic stripe 1718 (e.g., on the back side of the card 1700).

In some embodiments, the system card 1700 includes payment card functionalities (e.g., credit card, debit card, etc.). To accomplish this, the system 10 may offer payment card services inhouse, and/or may partner with existing credit card companies, banks, credit unions, lenders, etc., to offer payment card services through the existing credit card companies while providing the customer's medical records information (e.g., embedded in the microchip 1716, the magnetic stripe 1718, or elsewhere on the card). In such embodiments, a customer C may pay for access to a venue V (e.g., when a ticket must be purchased to enter the venue V) while simultaneously providing his/her medical record information via the same system card 1700.

In some embodiments, the system card 1700 is manufactured or otherwise produced using techniques as known in the art. In some embodiments, the card 1700 may be produced by taking at least some of the following actions:
1. Plastic compounding and molding of one or more layers using extrusion molds or other types of molding equipment;
2. Lamination of one or more layers together using lamination equipment;
3. Embedding of additional elements such as microchips using milling equipment;
4. Printing using dye sublimation equipment, silk screen printing equipment, or other types of printing equipment; and
5. Cutting and embossing using die cutting equipment or other types of equipment.

For the purposes of this specification, the molding equipment, lamination equipment, milling equipment, printing equipment, and cutting and embossing equipment will be referred to as system card production equipment.

It is understood that any aspect and/or element of any of the embodiments described herein or otherwise may be combined in any way to form additional embodiments easily understood by a person of ordinary skill in the art and all within the scope of the system 10. Those of ordinary skill in the art will appreciate and understand, upon reading this description, that embodiments hereof may provide different and/or other advantages, and that not all embodiments or implementations need have all advantages.

Computing

The services, mechanisms, operations and acts shown and described above are implemented, at least in part, by software running on one or more computers or computer systems or devices. It should be appreciated that each user device is, or comprises, a computer system.

Programs that implement such methods (as well as other types of data) may be stored and transmitted using a variety of media (e.g., computer readable media) in a number of manners. Hard-wired circuitry or custom hardware may be used in place of, or in combination with, some or all of the software instructions that can implement the processes of various embodiments. Thus, various combinations of hardware and software may be used instead of software only.

One of ordinary skill in the art will readily appreciate and understand, upon reading this description, that the various processes described herein may be implemented by, e.g., appropriately programmed general purpose computers, special purpose computers and computing devices. One or more such computers or computing devices may be referred to as a computer system.

Figure 11:
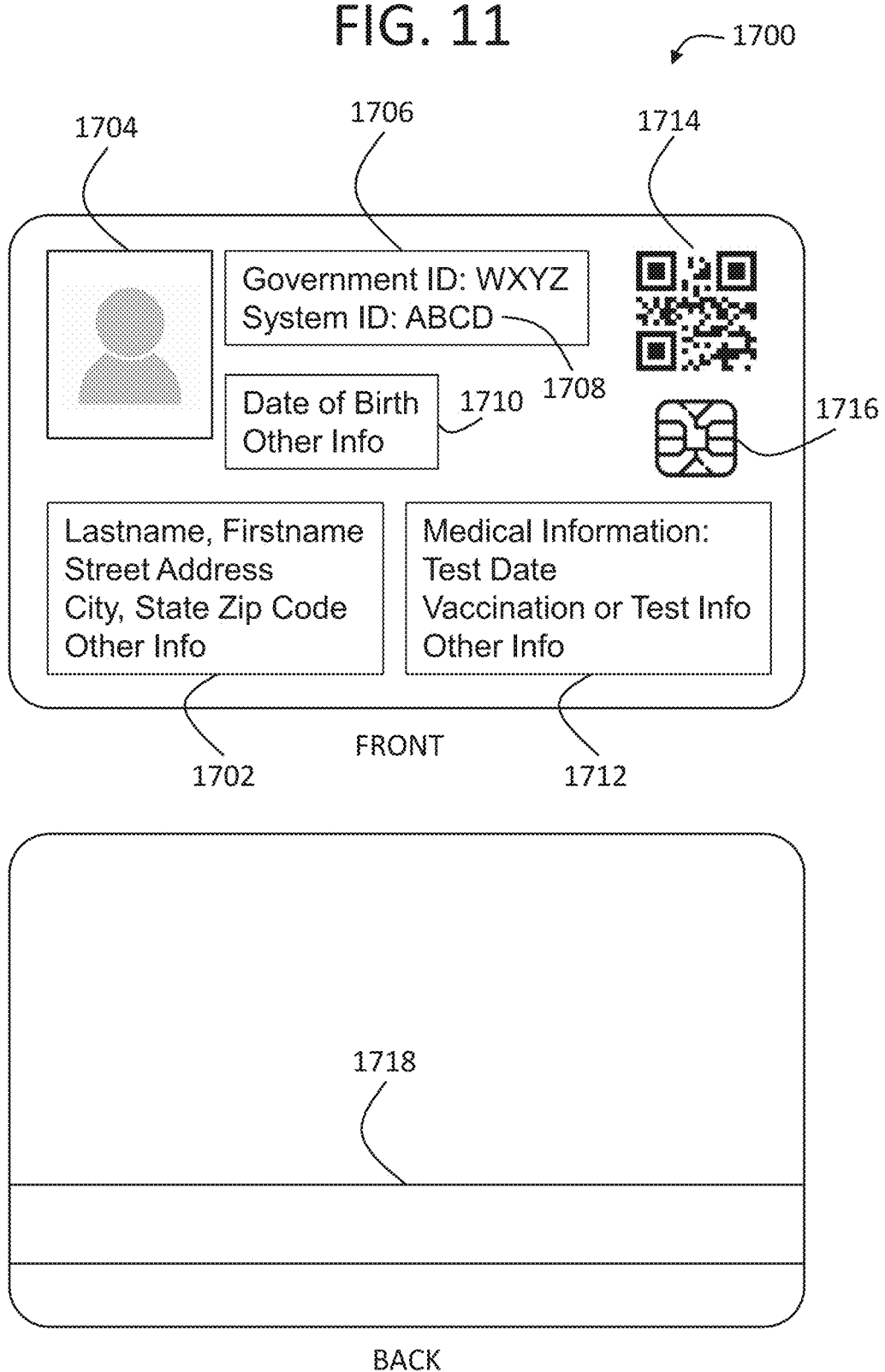
FIG. 11 shows aspects of a system identification card in accordance with exemplary embodiments hereof.

FIG. 11 is a schematic diagram of a computer system 1600 upon which embodiments of the present disclosure may be implemented and carried out.

According to the present example, the computer system 1600 includes a bus 1602 (i.e., interconnect), one or more processors 1604, one or more communications ports 1614, a main memory 1610, removable storage media 1610, read-only memory 1608, and a mass storage 1612. Communication port(s) 1614 may be connected to one or more networks by way of which the computer system 1600 may receive and/or transmit data.

As used herein, a "processor" means one or more microprocessors, central processing units (CPUs), computing devices, microcontrollers, digital signal processors, or like devices or any combination thereof, regardless of their architecture. An apparatus that performs a process can include, e.g., a processor and those devices such as input devices and output devices that are appropriate to perform the process.

Processor(s) 1604 can be (or include) any known processor, such as, but not limited to, an Intel® Itanium® or Itanium 2® processor(s), AMD® Opteron® or Athlon MP® processor(s), or Motorola® lines of processors, and the like. Communications port(s) 1614 can be any of an RS-232 port for use with a modem-based dial-up connection, a 10/100 Ethernet port, a Gigabit port using copper or fiber, or a USB port, and the like. Communications port(s) 1614 may be chosen depending on a network such as a Local Area Network (LAN), a Wide Area Network (WAN), a CDN, or any network to which the computer system 1600 connects. The computer system 1600 may be in communication with peripheral devices (e.g., display screen 1610, input device(s) 1618) via Input/Output (I/O) port 1620. Some or all of the peripheral devices may be integrated into the computer system 1600, and the input device(s) 1618 may be integrated into the display screen 1610 (e.g., in the case of a touch screen).

Main memory 1610 can be Random Access Memory (RAM), or any other dynamic storage device(s) commonly known in the art. Read-only memory 1608 can be any static storage device(s) such as Programmable Read-Only Memory (PROM) chips for storing static information such as instructions for processor(s) 1604. Mass storage 1612 can be used to store information and instructions. For example, hard disks such as the Adaptec® family of Small Computer Serial Interface (SCSI) drives, an optical disc, an array of disks such as Redundant Array of Independent Disks (RAID), such as the Adaptec® family of RAID drives, or any other mass storage devices may be used.

Bus 1602 communicatively couples processor(s) 1604 with the other memory, storage and communications blocks. Bus 1602 can be a PCI/PCI-X, SCSI, a Universal Serial Bus (USB) based system bus (or other) depending on the storage devices used, and the like. Removable storage media 1610 can be any kind of external hard-drives, floppy drives, IOMEGA® Zip Drives, Compact Disc-Read Only Memory (CD-ROM), Compact Disc-Re-Writable (CD-RW), Digital Versatile Disk-Read Only Memory (DVD-ROM), etc.

Embodiments herein may be provided as one or more computer program products, which may include a machine-readable medium having stored thereon instructions, which may be used to program a computer (or other electronic devices) to perform a process. As used herein, the term "machine-readable medium" refers to any medium, a plurality of the same, or a combination of different media, which participate in providing data (e.g., instructions, data structures) which may be read by a computer, a processor, or a like device. Such a medium may take many forms, including but not limited to, non-volatile media, volatile media, and transmission media. Non-volatile media include, for example, optical or magnetic disks and other persistent memory. Volatile media include dynamic random access memory, which typically constitutes the main memory of the computer. Transmission media include coaxial cables, copper wire and fiber optics, including the wires that comprise a system bus coupled to the processor. Transmission media may include or convey acoustic waves, light waves and electromagnetic emissions, such as those generated during radio frequency (RF) and infrared (IR) data communications.

The machine-readable medium may include, but is not limited to, floppy diskettes, optical discs, CD-ROMs, magneto-optical disks, ROMs, RAMs, erasable programmable read-only memories (EPROMs), electrically erasable programmable read-only memories (EEPROMs), magnetic or optical cards, flash memory, or other type of media/machine-readable medium suitable for storing electronic instructions. Moreover, embodiments herein may also be downloaded as a computer program product, wherein the program may be transferred from a remote computer to a requesting computer by way of data signals embodied in a carrier wave or other propagation medium via a communication link (e.g., modem or network connection).

Various forms of computer readable media may be involved in carrying data (e.g. sequences of instructions) to a processor. For example, data may be (i) delivered from RAM to a processor; (ii) carried over a wireless transmission medium; (iii) formatted and/or transmitted according to numerous formats, standards or protocols; and/or (iv) encrypted in any of a variety of ways well known in the art.

A computer-readable medium can store (in any appropriate format) those program elements that are appropriate to perform the methods.

As shown, main memory 1610 is encoded with application(s) 1622 that support(s) the functionality as discussed herein (an application 1622 may be an application that provides some or all of the functionality of one or more of the mechanisms described herein). Application(s) 1622 (and/or other resources as described herein) can be embodied as software code such as data and/or logic instructions (e.g., code stored in the memory or on another computer readable medium such as a disk) that supports processing functionality according to different embodiments described herein.

During operation of one embodiment, processor(s) 1604 accesses main memory 1610 via the use of bus 1602 in order to launch, run, execute, interpret or otherwise perform the logic instructions of the application(s) 1622. Execution of application(s) 1622 produces processing functionality of the service(s) or mechanism(s) related to the application(s). In other words, the process(es) 1624 represents one or more portions of the application(s) 1622 performing within or upon the processor(s) 1604 in the computer system 1600.

It should be noted that, in addition to the process(es) 1624 that carries (carry) out operations as discussed herein, other embodiments herein include the application 1622 itself (i.e., the un-executed or non-performing logic instructions and/or data). The application 1622 may be stored on a computer readable medium (e.g., a repository) such as a disk or in an optical medium. According to other embodiments, the application 1622 can also be stored in a memory type system such as in firmware, read only memory (ROM), or, as in this example, as executable code within the main memory 1610 (e.g., within Random Access Memory or RAM). For example, application 1622 may also be stored in removable storage media 1610, read-only memory 1008, and/or mass storage device 1612.

Those skilled in the art will understand that the computer system 600 can include other processes and/or software and hardware components, such as an operating system that controls allocation and use of hardware resources.

As discussed herein, embodiments of the present invention include various steps or operations. A variety of these steps may be performed by hardware components or may be embodied in machine-executable instructions, which may be used to cause a general-purpose or special-purpose processor programmed with the instructions to perform the operations. Alternatively, the steps may be performed by a combination of hardware, software, and/or firmware. The term "module" refers to a self-contained functional component, which can include hardware, software, firmware or any combination thereof.

One of ordinary skill in the art will readily appreciate and understand, upon reading this description, that embodiments of an apparatus may include a computer/computing device operable to perform some (but not necessarily all) of the described process.

Embodiments of a computer-readable medium storing a program or data structure include a computer-readable medium storing a program that, when executed, can cause a processor to perform some (but not necessarily all) of the described process.

Where a process is described herein, those of ordinary skill in the art will appreciate that the process may operate without any user intervention. In another embodiment, the process includes some human intervention (e.g., a step is performed by or with the assistance of a human).

As used in this description, the term "portion" means some or all. So, for example, "A portion of X" may include some of "X" or all of "X". In the context of a conversation, the term "portion" means some or all of the conversation.

As used herein, including in the claims, the phrase "at least some" means "one or more," and includes the case of only one. Thus, e.g., the phrase "at least some ABCs" means "one or more ABCs", and includes the case of only one ABC.

As used herein, including in the claims, the phrase "based on" means "based in part on" or "based, at least in part, on," and is not exclusive. Thus, e.g., the phrase "based on factor X" means "based in part on factor X" or "based, at least in part, on factor X." Unless specifically stated by use of the word "only", the phrase "based on X" does not mean "based only on X."

As used herein, including in the claims, the phrase "using" means "using at least," and is not exclusive. Thus, e.g., the phrase "using X" means "using at least X." Unless specifically stated by use of the word "only", the phrase "using X" does not mean "using only X."

In general, as used herein, including in the claims, unless the word "only" is specifically used in a phrase, it should not be read into that phrase.

As used herein, including in the claims, the phrase "distinct" means "at least partially distinct." Unless specifically stated, distinct does not mean fully distinct. Thus, e.g., the phrase, "X is distinct from Y" means that "X is at least partially distinct from Y," and does not mean that "X is fully distinct from Y." Thus, as used herein, including in the claims, the phrase "X is distinct from Y" means that X differs from Y in at least some way.

As used herein, including in the claims, a list may include only one item, and, unless otherwise stated, a list of multiple items need not be ordered in any particular manner. A list may include duplicate items. For example, as used herein, the phrase "a list of XYZs" may include one or more "XYZs".

It should be appreciated that the words "first" and "second" in the description and claims are used to distinguish or identify, and not to show a serial or numerical limitation. Similarly, the use of letter or numerical labels (such as "(a)", "(b)", and the like) are used to help distinguish and/or identify, and not to show any serial or numerical limitation or ordering.

No ordering is implied by any of the labeled boxes in any of the flow diagrams unless specifically shown and stated. When disconnected boxes are shown in a diagram the activities associated with those boxes may be performed in any order, including fully or partially in parallel.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

The invention claimed is:

1. A method of authenticating medical information comprising:
   (A) authenticating, by one or more computer systems, an identity of a first user using a secure cryptographic protocol;
   (B) receiving, by one or more computer systems, first biometric data from a biometric sensor associated with the first user;
   (C) associating, by one or more computer systems, the identity of the first user with the first biometric data using a secure data linkage process;
   (D) receiving, by one or more computer systems, at least one medical record related to the first user electronically transmitted from a healthcare provider system;
   (E) receiving, by one or more computer systems, second biometric data from the biometric sensor associated with the first user during the medical record transmission;
   (F) processing, by a biometric recognition system implemented in the one or more computer systems, the second biometric data to determine if it matches the first biometric data, wherein the biometric recognition system includes machine learning algorithms trained on biometric data patterns;
   (G) in response to determining, using the biometric recognition system, that the second biometric data matches the first biometric data in (F), then:
   (H) providing, using one or more computer systems, the at least one medical record to an authorized entity electronically authenticated by the first user.

2. The method of claim 1 wherein the biometric recognition system includes at least one of a facial recognition system and a fingerprint recognition system.

3. The method of claim 1 wherein the providing the at least one medical record in (H) includes providing the at least one medical record to a venue.

4. The method of claim 1 further comprising:
   (I) determining whether the at least one medical record meets a first requirement;
   (J) in response to a determination that the at least one medical records meets the first requirement, granting the first user access to a first venue.

5. The method of claim 1 wherein the at least one medical record includes at least one of vaccination information and viral anti-body test results.

6. The method of claim 4 wherein the first requirement includes at least one of a valid vaccination record and a positive viral anti-body test result.

7. The method of claim 1 wherein the providing the at least one medical record in (H) includes at least one of displaying the at least one medical record on a user device and providing a quick response (QR) code.

8. A method of authenticating medical information comprising:
- (A) receiving, via a secure communication channel, an encrypted alphanumeric character string from a first identification card associated with a first user;
- (B) decrypting the encrypted alphanumeric character string to obtain an identifier associated with the first user;
- (C) retrieving, from a secure medical records database, at least one medical record associated with the identifier;
- (D) generating, using card production equipment configured to operate based on the retrieved medical record, a first card that includes at least some information from the retrieved medical record, wherein the first card is configured for secure physical authentication.

9. The method of claim 8 wherein the information relating to a first alphanumeric character string on a first identification card includes at least one digit of a first driver's license number associated with the first user.

10. The method of claim 9 wherein the at least one digit of the first driver's license associated with the first user includes a total of the last four digits of the first driver's license number associated with the first user.

11. The method of claim 8 wherein the at least one medical record includes at least one of vaccination information and viral anti-body test results.

12. The method of claim 8 further comprising:
- (A)(1) receiving a first photograph of the first user;
- (A)(2) receiving contact information of the first user;
- (C)(1) printing the first photograph and/or the contact information on the first card.

13. The method of claim 8 further comprising:
- (C)(1) embedding a microchip into the first card;
- (C)(2) storing at least a portion of the at least one medical record onto the microchip.

14. The method of claim 8 further comprising:
- (C)(1) associating a quick response (QR) code with at least a portion of the at least one medical record;
- (C)(2) printing the QR code on the first card.

15. The method of claim 8 further comprising:
- (A)(1) associating a first system identification code with the first user;
- (C)(1) printing the first system identification code on the first card.

16. The method of claim 8 wherein the displaying of at least a portion of the at least one medical record in (C) includes displaying the at least a portion of the at least one medical record on a programmable digital readout embedded in the first card.

17. The method of claim 8 further comprising:
- (C)(1) providing a magnetic stripe on the first card;
- (C)(2) encoding at least a portion of the at least one medical record onto the magnetic stripe.

18. The method of claim 8 further comprising:
- (C)(1) associating the first card with a credit card services provider.

* * * * *